United States Patent
Ichim et al.

(10) Patent No.: US 11,229,674 B1
(45) Date of Patent: Jan. 25, 2022

(54) NUTRACEUTICALS FOR SUPPRESSING INDOLAMINE 2,3 DEOXYGENASE

(71) Applicants: Thomas E. Ichim, Oceanside, CA (US); Timothy G. Dixon, Oceanside, CA (US); James Veltmeyer, Oceanside, CA (US)

(72) Inventors: Thomas E. Ichim, Oceanside, CA (US); Timothy G. Dixon, Oceanside, CA (US); James Veltmeyer, Oceanside, CA (US)

(73) Assignee: Therapeutic Solutions International, Inc., Oceanside, CA (US)

( * ) Notice: Subject to any disclaimer, the term of this patent is extended or adjusted under 35 U.S.C. 154(b) by 0 days.

(21) Appl. No.: 16/901,028

(22) Filed: Oct. 23, 2020

(51) Int. Cl.
| | |
|---|---|
| *A61K 36/82* | (2006.01) |
| *A61K 36/31* | (2006.01) |
| *A61P 29/00* | (2006.01) |
| *A61K 36/45* | (2006.01) |
| *A61K 36/71* | (2006.01) |

(52) U.S. Cl.
CPC .............. *A61K 36/82* (2013.01); *A61K 36/31* (2013.01); *A61K 36/45* (2013.01); *A61K 36/71* (2013.01); *A61P 29/00* (2018.01)

(58) Field of Classification Search
CPC ...... A61K 31/436; A61K 35/15; A61K 35/51; A61K 47/44; A61K 9/0014; A61K 36/82; A61K 36/31; A61K 36/45; A61K 36/71; A61L 2300/30; A61L 27/3834; A61L 27/3895; A61L 27/54; A61P 11/00; A61P 11/06; A61P 11/08; A61P 13/00; A61P 15/00; A61P 15/08; A61P 15/10; A61P 17/00; A61P 17/02; A61P 17/06; A61P 17/08; A61P 29/00
See application file for complete search history.

(56) References Cited

PUBLICATIONS

Grant R and Kapoor V "Inhibition of indoleamine 2,3-dioxygenase activity in IFN-γ stimulated astroglioma cells decreases intracellular NAD levels" Biochemical Pharmacology 66 (2003) 1033-1036; doi:10.1016/S0006-2952(03)00464-7 (Year: 2003).*

* cited by examiner

*Primary Examiner* — Aaron J Kosar
(74) *Attorney, Agent, or Firm* — Baumgartner Patent Law; Marc Baumgartner

(57) ABSTRACT

Disclosed are compositions of matter, treatments and protocols useful for reduction of expression and/or activity of indolamine 2,3 deoxygenase (IDO). In some embodiments the invention teaches the administration of a therapeutic combination of ingredients comprising of pterostilbene, *Nigella sativa*, sulforaphane, and epigallocatechin-3-gallate (EGCG) to a mammal at possessing an increased expression and/or activity of said IDO in which reduction of number and/or activity is desired. In another embodiment, the invention teaches administration of said therapeutic combination to a mammal infected with viral and/or bacterial infections and/or neoplasia. In some embodiments dosage of said therapeutic combination is based on inflammatory and/or immunological parameters observed in patients.

19 Claims, 1 Drawing Sheet

NUTRACEUTICALS FOR SUPPRESSING INDOLAMINE 2,3 DEOXYGENASE

FIELD OF THE INVENTION

The invention pertains to the field of immunotherapy, more specifically, the invention pertains to the use of natural compounds to elicit immune modulation, more specifically, the invention pertains to the field of reducing IDO expression and/or activity through administration of natural compounds.

BACKGROUND OF THE INVENTION

It is known that tryptophan (Trp) is an essential amino acid required for the biosynthesis of proteins, niacin and the neurotransmitter 5-hydroxytryptamine (serotonin). The enzyme indoleamine 2,3-dioxygenase (also known as INDO, IDO or IDO1) catalyzes the first and rate limiting step in the degradation of L-tryptophan to N-formyl-kynurenine. In human cells, a depletion of Trp resulting from IDO activity is a prominent gamma interferon (IFN-.gamma.)-inducible antimicrobial effector mechanism. IFN-.gamma. stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process.

Recently, an immunoregulatory role of Trp depletion has received much attention. Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients. To this end, it has recently been shown that IDO inhibition can enhance the levels of virus-specific T cells and, concomitantly, reduce the number of virally-infected macrophages in a mouse model of HIV.

It is known that IDO plays a role in the immunosuppressive processes that prevent fetal rejection in utero. More than 40 years ago, it was observed that, during pregnancy, the genetically disparate mammalian conceptus survives in spite of what would be predicted by tissue transplantation immunology. Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to 1MT, and a rapid, T cell-induced rejection of all allogeneic concept was observed. Thus, by catabolizing tryptophan, the mammalian conceptus appears to suppresses T-cell activity and defends itself against rejection, and blocking tryptophan catabolism during murine pregnancy allows maternal T cells to provoke fetal allograft rejection.

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor. It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies.

SUMMARY

Preferred embodiments are directed to methods of inhibiting number and/or activity of indolamine 2,3 deoxygenase (IDO) comprising administration of a therapeutic combination comprising of: a) Green Tea and/or extract thereof; b) Blueberry and/or extract thereof; c) *Nigella sativa* and/or extract thereof; and d) broccoli and/or extract thereof.

Further methods include embodiments wherein said green tea extract is epigallocatechin-3-gallate or an analogue thereof.

Further methods include embodiments wherein said blueberry extract is pterostilbene or an analogue thereof.

Further methods include embodiments wherein said *Nigella sativa* extract is thymoquinone or an analogue thereof.

Further methods include embodiments wherein said broccoli extract is sulforaphane or an analogue thereof.

Further methods include embodiments wherein said therapeutic combination is administered at a dosage and frequency sufficient to inhibit IDO expression and/or activity.

Further methods include embodiments wherein inhibition of IDO expression and/or activity in the host is associated with enhancement of natural killer cell activity.

Further methods include embodiments wherein said natural killer cell activity is quantified by ability to lyse a virally infected cell.

Further methods include embodiments wherein said natural killer cell activity is quantified by ability to lyse K562 cells.

Further methods include embodiments wherein said natural killer cell activity is quantified by ability to lyse YAC-1 cells.

Further methods include embodiments wherein inhibition of IDO expression and/or activity in the host is associated with enhancement of interferon production.

Further methods include embodiments wherein inhibition of IDO expression and/or activity in the host is accomplished by enhancement of T cell activation.

Further methods include embodiments wherein said T cell activation is induction of T helper cell 1 activity.

Further methods include embodiments wherein said T helper cell 1 activity comprises production of interferon gamma.

Further methods include embodiments wherein said T cell activation is induction of T cytotoxic cell activity.

Further methods include embodiments wherein said therapeutic combination is administered at a dosage and frequency sufficient to suppress growth of a tumor.

Further methods include embodiments wherein said tumor growth in the host is associated with suppression of cancer angiogenesis.

Further methods include embodiments wherein said cancer angiogenesis comprises of: a) endothelial cell detachment; b) migration towards a chemotactic gradient; and c) tube formation.

Further methods include embodiments wherein said therapeutic mixture decreases tumor associated fibroblasts.

Further methods include embodiments wherein said tumor associated fibroblasts secrete immune suppressive factors.

Further methods include embodiments wherein said immune suppressive factors are interleukin-4.

Further methods include embodiments wherein said immune suppressive factors are interleukin-10.

Further methods include embodiments wherein said immune suppressive factors are interleukin-13.

Further methods include embodiments wherein said immune suppressive factors are interleukin-20.

Further methods include embodiments wherein said immune suppressive factors are TGF-beta.

Further methods include embodiments wherein said immune suppressive factors are HGF.

Further methods include embodiments wherein said immune suppressive factors are VEGF.

Further methods include embodiments wherein said immune suppressive factors are PDGF.

Further methods include embodiments wherein said immune suppressive factors are FGF-1.

Further methods include embodiments wherein said immune suppressive factors are FGF-2.

Further methods include embodiments wherein said immune suppressive factors are PGE-2.

Further methods include embodiments wherein said immune suppressive factors are soluble HLA-G.

Further methods include embodiments wherein said tumor associated fibroblasts inhibit and/or kill immune system cells.

Further methods include embodiments wherein said immune system cells are T cells.

Further methods include embodiments wherein said T cells are CD4 T cells.

Further methods include embodiments wherein said T cells are CD4 T cells capable of secreting more interferon gamma as compared to interleukin-4.

Further methods include embodiments wherein said T cells are Th1 cells.

Further methods include embodiments wherein said T cells are CD8 T cells.

Further methods include embodiments wherein said T cells are cytotoxic T cells.

Further embodiments are directed to treating COVID-19 comprising administration of one or more interferons together with a therapeutic combination comprising of: a) Green Tea and/or extract thereof; b) Blueberry and/or extract thereof; c) *Nigella sativa* and/or extract thereof; and d) broccoli and/or extract thereof.

Further methods include embodiments wherein said green tea extract is epigallocatechin-3-gallate or an analogue thereof.

Further methods include embodiments wherein said blueberry extract is pterostilbene or an analogue thereof.

Further methods include embodiments wherein said *Nigella sativa* extract is thymoquinone or an analogue thereof.

Further methods include embodiments wherein said broccoli extract is sulforaphane or an analogue thereof.

Further methods include embodiments wherein said therapeutic combination is administered at a dosage and frequency sufficient to inhibit IDO expression and/or activity.

Further methods include embodiments wherein said interferon is interferon alpha.

DETAILED DESCRIPTION OF THE INVENTION

Figure 1:
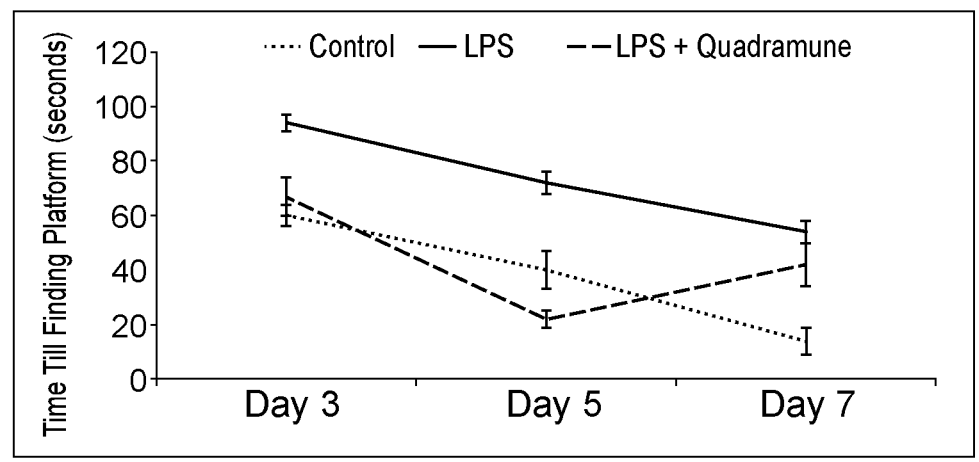
FIG. 1 is a line graph showing QUADRAMUNE™ Preserves Memory in Inflammation Associated Memory Decline Model

The invention discloses use of QUADRAMUNE™, a composition of pterostilbene, *Nigella sativa* extract, green tea extract, and broccoli for reduction in activity of indolamine 2,3 deoxygenase, and specifically, reduction of inflammation associated immune suppression, memory loss, and depression.

A composition in accordance with the present invention containing pterostilbene, thymoquinone, EGCG, and sulforaphane, or a pharmaceutically acceptable salt thereof, can be prepared by conventional procedures for blending and mixing compounds. Preferably, the composition also includes an excipient, most preferably a pharmaceutical excipient. Compositions containing an excipient and incorporating the pterostilbene can be prepared by procedures known in the art. For example, the ingredients can be formulated into tablets, capsules, powders, suspensions, solutions for oral administration and solutions for parenteral administration including intravenous, intradermal, intramuscular, and subcutaneous administration, and into solutions for application onto patches for transdermal application with common and conventional carriers, binders, diluents, and excipients.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

We disclose that the invention further provides nutraceutical compositions comprising the chemical compound of the invention, or a pharmaceutically acceptable salt or derivative thereof, together with one or more nutraceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof. An oral composition can generally include an inert diluent or an edible carrier. The nutraceutical composition can comprise a functional food component or a nutrient component. The term "functional food" refers to a food which contains one or a combination of components which affects functions in the body so as to have positive cellular or physiological effects. The term "nutrient" refers to any substance that furnishes nourishment to an animal.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid, which is in a mixture with the finely divided active component. In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

Liquid preparations include solutions, suspensions, and emulsions, for example, water or water-propylene glycol solutions. For example, parenteral injection liquid preparations can be formulated as solutions in aqueous polyethylene glycol solution. The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavors, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Compositions suitable for topical administration in the mouth include lozenges comprising the active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In compositions intended for administration to the respiratory tract, including intranasal compositions, the compound will generally have a small particle size for example of the order of 5 microns or less. Such a particle size may be obtained by means known in the art, for example by micronization.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets, capsules and lozenges for oral administration and liquids for intravenous administration and continuous infusion are preferred compositions. Solutions or suspensions for application to the nasal cavity or to the respiratory tract are preferred compositions. Transdermal patches for topical administration to the epidermis are preferred.

Details on techniques for formulation and administration may be found in the latest edition of Remington's Pharmaceutical Sciences (Maack Publishing Co., Easton, Pa.).

A therapeutically effective dose refers to that amount of active ingredient, which ameliorates the symptoms or condition. Therapeutic efficacy and toxicity, e.g. ED.sub.50 and LD.sub.50, may be determined by standard pharmacological procedures in cell cultures or experimental animals. The dose ratio between therapeutic and toxic effects is the therapeutic index and may be expressed by the ratio LD.sub.50/ED.sub.50. Pharmaceutical compositions exhibiting large therapeutic indexes arepreferred.

The dosage of compound used in accordance with the invention varies depending on the compound and the condition being treated. The age, lean body weight, total weight, body surface area, and clinical condition of the recipient patient; and the experience and judgment of the clinician or practitioner administering the therapy are among the factors affecting the selected dosage. Other factors include the route of administration, the patient's medical history, the severity of the disease process, and the potency of the particular compound. The dose should be sufficient to ameliorate symptoms or signs of the disease treated without producing unacceptable toxicity to the patient. The dosage may be varied by titration of the dosage to the particular circumstances of this invention to produce the desired therapeutic effect.

Example 1: QUADRAMUNE™ Preserves Memory in Inflammation Associated Memory Decline Model Female BALB/c mice were treated with control, daily LPS treatment, and some with LPS and QUADRAMUNE™. QUADRAMUNE™ was administered daily by gavage at a concentration 1 (100 ug of broccoli sprout extract, *Nigella sativa*, and green tea extract, and 50 ug of pterostilbene), and concentration 2 (200 ug of broccoli sprout extract, *Nigella sativa*, and green tea extract, and 100 ug of pterostilbene).

To assess memory function, water filled basin which was 120 cm in diameter was broken into 4 quadrants. 10 cm diameter platform placed 1 cm below water. Mice were forced to swim to find the hidden platform, starting from all four different quadrants, each day for 7 days. The time was recorded if they could find the hidden platform in 60 s . . . . If not, mice are guided toward the platform and allowed to stand on it for 10 s. Results are shown in FIG. 1.

Example 2: QUADRAMUNE™ Reduces Inflammation Associated Kynurenine Elevation

Figure 2:
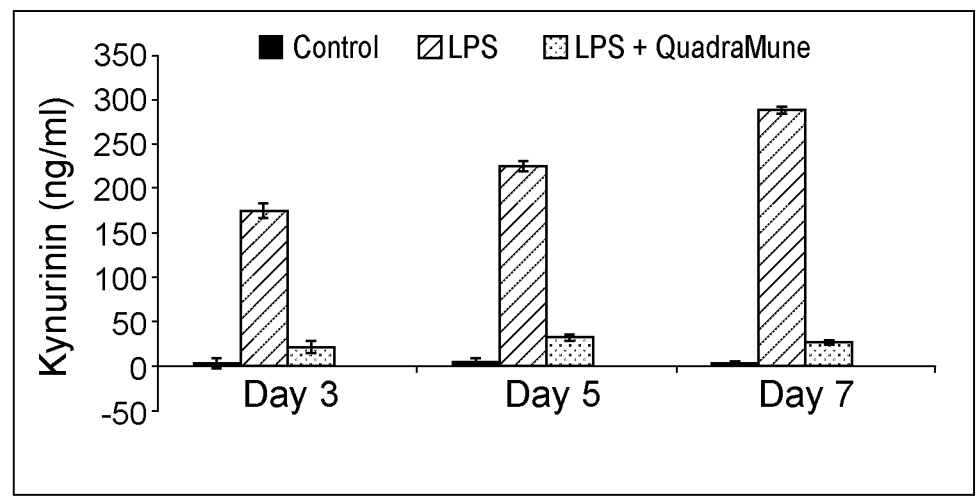
FIG. 2 is a bar graph showing QUADRAMUNE™ Reduces Inflammation Associated Kynurenine Elevation

Blood samples were collected from mice in Example 1 and assessed for Kynurenine content. Augmented levels of kynurenine were observed in LPS treated mice as compared to controls. Results are shown in FIG. 2.

The invention claimed is:

1. A method of inhibiting indolamine 2,3 deoxygenase (IDO) expression or activity, comprising: administration to a patient in need a therapeutic combination comprising: a) Green Tea and/or extract thereof; b) Blueberry and/or extract thereof; c) *Nigella sativa* and/or extract thereof; and d) broccoli and/or extract thereof.

2. The method of claim 1, wherein said green tea extract is epigallocatechin-3-gallate or an analogue thereof.

3. The method of claim 1, wherein said blueberry extract is pterostilbene or an analogue thereof.

4. The method of claim 1, wherein said *Nigella sativa* extract is thymoquinone or an analogue thereof.

5. The method of claim 1, wherein said broccoli extract is sulforaphane or an analogue thereof.

6. The method of claim 1, wherein inhibition of IDO expression and/or activity in the host is associated with enhancement of natural killer cell activity.

7. The method of claim 6, wherein said natural killer cell activity is quantified by ability to lyse a virally infected cell.

8. The method of claim 6, wherein said natural killer cell activity is quantified by ability to lyse K562 cells.

9. The method of claim 6, wherein said natural killer cell activity is quantified by ability to lyse YAC-1 cells.

10. The method of claim 1, wherein inhibition of IDO expression and/or activity in the host is associated with enhancement of interferon production.

11. The method of claim 1, wherein inhibition of IDO expression and/or activity in the host is accomplished by enhancement of T cell activation.

12. The method of claim 11, wherein said T cell activation is induction of T helper cell 1 activity.

13. The method of claim 12, wherein said T helper cell 1 activity comprises production of interferon gamma.

14. The method of claim 11, wherein said T cell activation is induction of T cytotoxic cell activity.

15. The method of claim 1, wherein said patient is suffering from a tumor, and said therapeutic combination is administered at a dosage and frequency sufficient to suppress growth of a tumor.

16. The method of claim 15, wherein said tumor growth in the host is associated with suppression of cancer angiogenesis.

17. The method of claim 1, wherein said patient is suffering from COVID 19.

18. The method of claim 1, wherein the patient is suffering from memory loss.

19. The method of claim 1, wherein the patient has elevated levels of Kynurenine.

* * * * *